United States Patent [19]
Eberly

[11] 4,412,743
[45] Nov. 1, 1983

[54] OFF-AXIS LIGHT BEAM DEFECT DETECTOR

[75] Inventor: Carlyle J. Eberly, Long Beach, Calif.

[73] Assignee: Discovision Associates, Costa Mesa, Calif.

[21] Appl. No.: 300,364

[22] Filed: Sep. 8, 1981

[51] Int. Cl.³ ............................................. G01N 21/88
[52] U.S. Cl. .................................. 356/237; 356/371; 369/45
[58] Field of Search ............... 356/123, 125, 371, 237, 356/373; 250/562, 563, 572; 358/342; 369/44, 45, 46, 111

[56] References Cited

U.S. PATENT DOCUMENTS 4,030,835 6/1977 Firester et al. ............... 356/237 X
4,085,423 4/1978 Tsunoda et al. .................... 369/45

FOREIGN PATENT DOCUMENTS

54-39103 3/1979 Japan .................................. 369/46

Primary Examiner—William L. Sikes
Assistant Examiner—Matthew W. Koren
Attorney, Agent, or Firm—Ronald J. Clark

[57] ABSTRACT

A method and apparatus for detecting a property such as a defect in a surface to be scanned. A focusing, or objective lens is provided together with a subsystem for maintaining a substantially fixed distance between the focusing lens and the scanned surface. Scanning is effected by providing lateral movement between the lens and the surface. An off-axis light beam source is provided having a beam of light which is directed to pass through the lens to the scanned surface. A light beam sensing element is positioned so as to detect that portion of the light beam reflected off of the surface and transmitted back through the lens.

17 Claims, 7 Drawing Figures

OFF-AXIS LIGHT BEAM DEFECT DETECTOR

BACKGROUND OF THE INVENTION

1. Field of the Invention

The present invention relates to light beam scanning apparatus, and more particularly relates to apparatus for detecting defects in information discs such as optical discs.

2. Brief Description of the Prior Art

An optical disc is a clear plastic disc approximately the size of a standard LP phonograph record, which has a thin reflective layer imbedded in its interior. The reflective layer is provided with a spiral-shaped information track in the form of a series of spaced-apart indicia, such as pits or holes, which can be "read" by a focused laser beam by directing the focused spot of the laser beam along the spiral-shaped track and detecting the variations in the intensity of the light reflected therefrom as the spot encounters alternately indicia and the reflective surface between the indicia. A detailed description of such a disc, in which the indicia are holes may be found in U.S. Pat. No. 4,264,911 which issued on Apr. 28, 1981 to Richard L. Wilkinson.

The size and spacing of the indicia, and the spacing of adjacent spiral tracks in a typical optical disc are extremely small, being of the order of magnitude of approximately one micron. In order to "read" the information contained in the indicia of such extremely small dimensions, the reading laser must be focused to an extremely small spot, being also of the order of magnitude of one micron.

Hole-type indicia can be formed in the reflective layer by means of a high intensity "writing" laser which is focused onto the layer and turned on and off as it it directed across the disc in spiral fashion. When the writing laser is turned on, it causes a hole to form in the reflective layer where it is focused, and when it is turned off it leaves the layer unaffected. Information can be imparted to the track by controlling the length and spacing of the holes.

In reading optical discs, whether of the "hole" type or the "pit" type, the reflected light of the reading laser is directed to a photo detector where the variation in intensity of the light incident on the photo detector due to the presence and absence of indicia in the reading track cause the output signal of the photo detector to take the form of a series of pulses. The length and spacing in time of these pulses correspond to the length and spacing of the indicia on the optical disc, and in this way the recorded information is recovered.

In both reading and writing it is necessary to maintain the laser spot in focus on the surface of the reflective layer. In both operations this is accomplished typically by means of a separate servo system which controls the position of an objective lens over the surface of the disc.

A description of an optical disc player including a disclosure of a technique for maintaining a laser beam focused to an appropriately small spot on an optical disc as it is "played" on the device may be found in U.S. Pat. No. 4,332,022, issued May 25, 1982, and commonly assigned to the assignee of the present invention.

The player apparatus disclosed in that application is designed especially to play video optical discs that contain video information for storage and playback of television program material. Briefly, the technique disclosed therein for maintaining the focus of the spot of laser light on the disc involves the provision of a separate beam of laser light substantially parallel to the reading laser light beam. This separate laser beam is focused onto the disc by the same optical system used to focus the read beam. The light of the separate laser beam is reflected off of the laser disc and directed to a special photo detector which detects the size of the beam incident thereon and provides an output signal indicative of the state of focus of the separate light beam. This output signal is used in a focus servo mechanism to maintain the separate beam in a focused condition even if the disc is warped. This also maintains the read beam in focus.

Such a focus servo system is used in writing apparatus as well.

It has been discovered, however, that the presence of certain kinds of defects in the reflective surface of the video optical disc, namely "dimples" and "inclusions", can cause the focus servo system to exceed its limits and thereby cause the optical system to lose focus, with consequent loss of information storage or retrieval, as the case may be. In the case of video disc playback, this can result in the temporary disruption of the video picture, frame skipping, and jump back, all of which are unacceptable from a commercial standpoint.

Since such defects are typically too small to be seen with the naked eye, visual inspection is an inadequate technique. In addition, not all defects give rise to disruptions of an unacceptable nature. Consequently, the technique utilized in the commercial production of optical video discs involves simply playing all or part of the disc and looking for any disturbances in the video picture which are considered unacceptable. However, if the entire disc is played, this is highly costly in man-hours. If only a part of the disc is played, however, not all defects will be detected.

It will therefore be appreciated that there is a need for an apparatus for detecting defects in optical discs which permits the rapid identification and location of defects in conjunction with a player apparatus to enable the rapid and selective playing of only those areas of the disc suspected of being defective to determine if an unacceptable defect exists at that area.

In the case of computer data storage and retrieval, if a defect is known to exist on the reflective layer of an optical disc, a special code can be inserted into the information track immediately in advance of the defect which will cause the information reading apparatus to stop looking for information for the period of time it takes the read beam to pass over the defect. Data retrieval can then be resumed, and in this way no information is lost. Thus, optical discs having defects can be used to store computer data for retrieval if the location and size of defects can be accurately determined in conjunction with an apparatus for storing the information on the disc.

It will therefore be appreciated there is is a need for a defect detecting apparatus which provides accurate indentification of the location and size of defects in optical discs. Further, there is a need for a defect detector apparatus which provides accurate detection of defects in conjunction with a laser writing function for an optical disc to permit the precise localization of the writing laser beam in advance of the defective area.

The present invention fulfills the aforementioned needs.

SUMMARY OF THE INVENTION

The present invention is embodied in a beam-scanning apparatus for detecting a property of a light beam reflected off of a surface to be scanned, which may be used in connection with another light beam scanning apparatus, for example, by way of retrofit to an existing apparatus. Included in the apparatus of the present invention is a focusing, or objective lens disposed above a surface to be scanned and means for maintaining a substantially fixed distance between the focusing lens and the scanning surface. Also included are scanning means for providing lateral movement between the lens and the surface. A light beam source is provided arranged to provide a light beam which is off-axis with respect to the central axis of the lens, wherein the light beam is directed to pass through the lens to the scanned surface. A light beam sensing element is positioned so as to detect that portion of the light beam reflected off of the surface and transmitted back through the lens.

More particularly, the scanning apparatus of the present invention is especially adaptable for use in connection with a video disc playback apparatus. Such playback apparatus typically includes a laser beam servo system for maintaining a focusing lens in a substantially fixed relationship with respect to a video disc being read. The apparatus of the present invention may be easily retrofitted to such video disc playback machine so as to use the focusing lens already provided in the system as well as other optical elements provided in the apparatus such as mirrors, quarter wavelength plates, and beam splitters to provide an accurate and rapid defect detecting function with respect to a video optical disc. The player may be quickly directed to the detected defective area for playback over the area to determine if the area provides acceptable playback.

Another use to which the apparatus of the present invention is especially adapted is in connection with a digital data recording apparatus to permit the accurate detection of the size and location of defects in the recording medium surface so that in response thereto, the recording of data in the areas where defects have been detected can be inhibited, and appropriate flag codes can be provided in the information track which informs the digital data reading machine not to look for data as it passes over the defective location.

In this connection, existing optical elements of the information recording apparatus may be used as well for the apparatus of the present invention.

Other aspects and advantages of the present invention will become apparent from the following description of the preferred embodiment, taken in conjunction with the accompanying drawings, which disclose by way of example, the principles of the invention.

DETAILED DESCRIPTION OF THE PREFERRED EMBODIMENT

Figure 1:
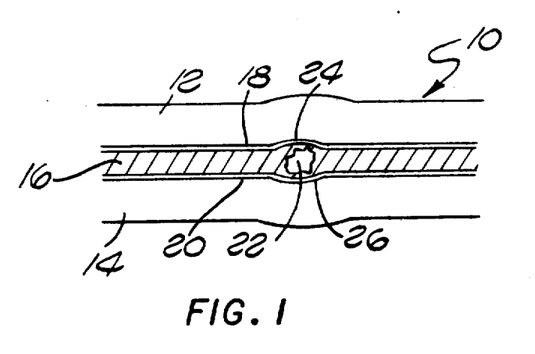
FIG. 1 is a partial cross section of an optical information recording disc depicting an inclusion-type defect therein.

FIG. 1 is a cross sectional diagram of a portion of an optical disc 10 which shows an "inclusion" type defect. The disc 10 is made of two clear plastic disc parts 12 and 14 which are bonded together with a layer of adhesive 16. Each of the disc's parts 12, 14, is provided with a layer of reflective material 18, 20 as shown. The information tracks described above are formed in these layers 18, 20 in a completed disc according to one of several different known processes.

A small particle of contaminating material 22 is present in the adhesive layer 16 between the parts 12, 14. Such a particle can be introduced in the manufacturing process in a number of ways, for example, if a dust particle lands on the adhesive prior to the bonding together of the disc parts. The presence of the particle 22 results in an inclusion which causes bulging areas 24, 26 of the reflective layers 18, 20. If the slope of the sides of such a bulge is great enough the focused servo system cannot maintain focus in the vicinity of the bulge and the aforementioned problems arise. Other kinds of defects causing similar sloped surfaces in the reflective layers 18, 20 may also be present in the disc 10.

Figure 2:
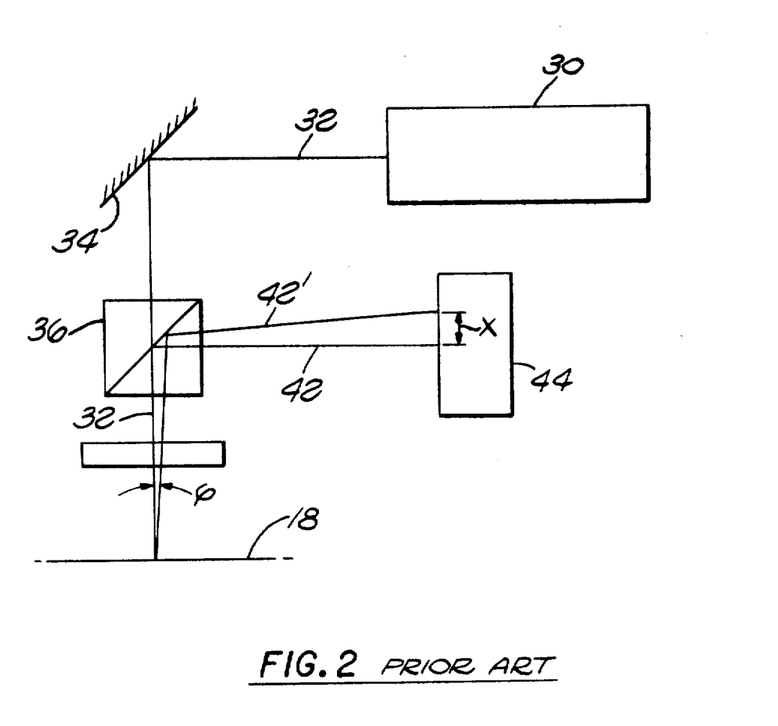
FIG. 2 is a schematic diagram of a prior art laser beam defect detecting apparatus.

One prior art arrangement which was devised in order to detect the presence of of such defects is depicted in FIG. 2. A laser 30 provides a polarized laser light beam output 32 which is directed to a mirror 34 where it is reflected to pass through a polarizing beam splitter 36. The light beam then passes through a quarter wavelength plate 38 before being reflected off of the surface 18, which is made to move laterally with respect to the beam 32. The incident beam 32 is directed perpendicularly with respect to the plane of the surface 18. Therefore, if the surface 18 contains no irregularities, the reflected beam 42 will be directed back along the same path to the polarizing beam splitter 36 after passing again through the quarter wavelength plate 38. After thus passing twice through the quarter wavelength plate 38, the light beam 42 is rotated 90° with respect to the incident light beam 32. Therefore, substantially all of the reflected light beam 42 will be reflected by the beam splitter 36 as shown.

As described above in connection with FIG. 1, the sides of the defect present a reflective surface which is oriented at an angle with respect to the plane of the reflective surface 18. Consequently, when the incident beam 32 of the apparatus of FIG. 3 encounters such a defect it is not reflected back along the same path, but rather it is reflected at some angle with respect to the incident path. Such a beam 42' is reflected off of the beam splitter 36 in a different direction. A position-sensitive photo detector 44 is placed along the path of the light beams 42, 42' reflected off of the beam splitter 36 and a signal is derived which is representative of the displacement x of the reflected beam 42'. Since the distance of x shown in FIG. 3 corresponds geometrically to the angle Φ of the reflected beam 42' with respect to the reflected beam 32 the output signal of the photodetector provides a measure of the presence of a defect.

Such an arrangement has proven effective in detecting defects in optical discs.

However, such an apparatus is not readily adaptable to provide a spot of light for defect detection close enough to the "read" laser spot or "write" laser spot in a reading or recording apparatus for desired accuracy of detection of defect location and size with respect to the primary (reading or writing) laser spot. For example, it is desired to place the defect detecting laser spot approximately 0.1 to 0.2 mm from the primary laser spot in the case of a video playback device in order to obtain the highest possible accuracy of detection of the location of defects with respect to the primary laser beam spot while at the same time providing sufficient lead of the defect detecting spot on the disc in advance of the primary laser beam spot to permit automatic switching without overshoot from a fast scan mode to a play mode within the response time of the player.

However, the objective lens and objective lens motion assembly used in the focus servo system are relatively large and must be placed close to the disc; a typical objective lens is about 8 mm in diameter and typically rides approximately 3 mm above the surface of the disc. The objective lens motion assembly surrounds the lens, further extending the diameter of the arrangement. These elements thus present a problem in adapting the arrangement of FIG. 2 to an optical recorder playback apparatus so as to provide defect detection with desired closeness to the primary laser beam spot.

Figure 3:
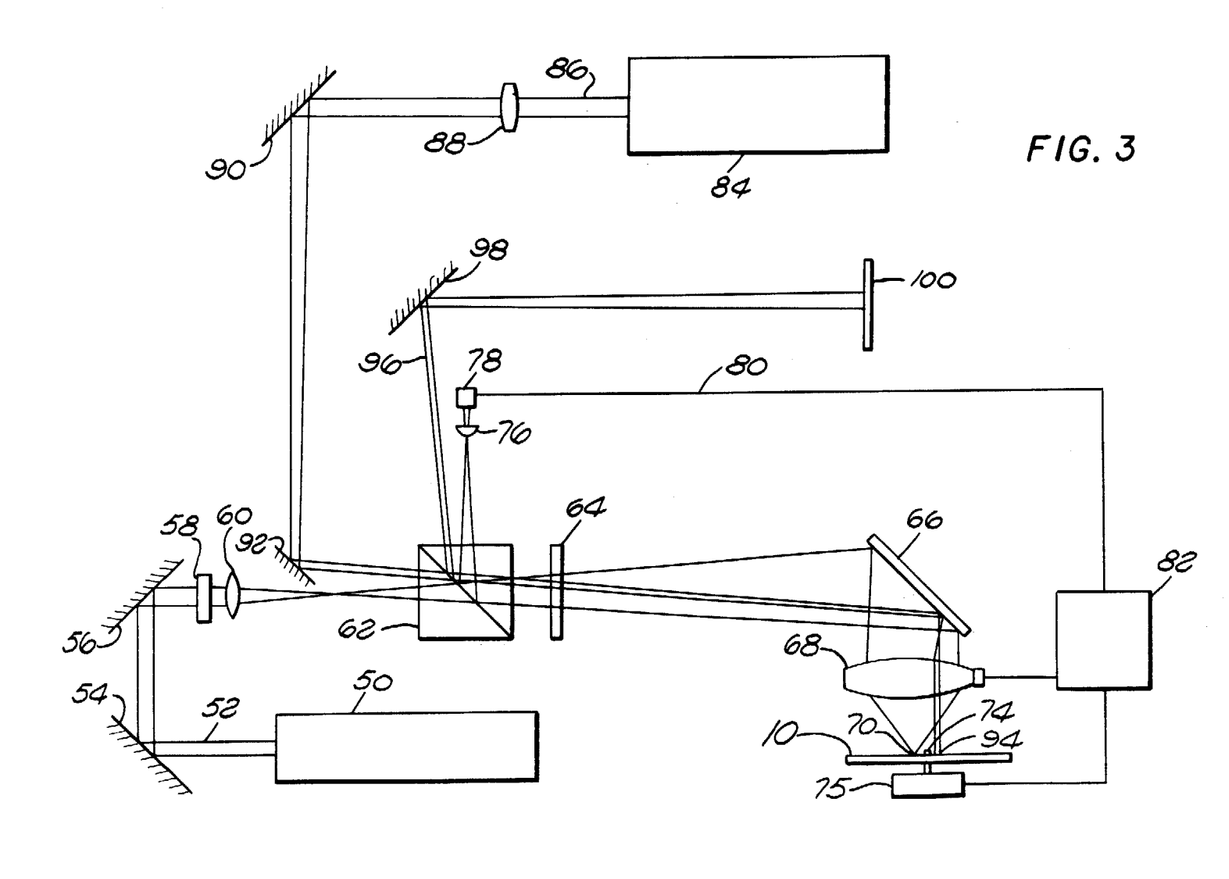
FIG. 3 is a schematic diagram of a laser beam defect detecting apparatus according to the principles of the present invention.

FIG. 3 of the drawings shows in block diagram form the preferred embodiment of the present invention. In accordance with this embodiment of the invention a standard video disc player apparatus has been modified to include the off-axis light beam defect detector of the present invention. A first laser beam source 50 is provided which emits a polarized beam of coherent light 52. This beam of light 52 is reflected off of mirrors 54 and 56 through a diffraction grating 58 and beam diverting lens 60 to a polarization beam splitter 62. The polarization of the light beam 52 is oriented so that a substantial portion of the beam passes through the beam splitter. The laser light 52 which passes through the beam splitter 62 is directed through a quarter wavelength plate 64 to a further mirror 66 wherein it is directed to an objective lens 68. The objective lens 68 focuses the diverging beam of laser light 52 to a spot 70 on the surface of a video disc 10. The video disc 10 is clamped to a spindle 74 which is rotated at high speeds by a spindle drive system 75 so that, in conjunction with a linear tracking mechanism associated with the objective lens (not shown) a spiral tracking function may be effected for the spot 70 of laser light on the disc 72, as is well known in the art. The light 52 is reflected back from the disc through the objective lens 68 where it is reflected off of mirror 66 and directed back through quarter wavelength plate 64 to the polarizing beam splitter 52. Because the reflected light directed to the beam splitter 62 passes through the quarter wavelength plate 64 twice the direction of polarization is rotated by 90° with respect to the incident light 52. Therefore, a substantial portion of the reflected light will be reflected by the beam splitter 62 at right angles to the central axis of the incident light beam due to the orientation of the surface of the beam splitter 62 as shown.

A focusing lens 76 is placed in the path of the light which has been reflected by the beam splitter 62 to focus that light onto a photodetector 78. The photodetector 78 may be arranged so as to provide an output signal representative of the state of focus of the spot 70 of light with respect to the video disc 10. Such output signal may be provided on a signal line 80 to a servo control mechanism 82 which, in response to the signal on line 80 maintains a relative spacing between the objective lens 68 and the disc 10 so as to maintain the spot of light 60 in focus on the reflective surface of the disc 10.

The construction and operation of the foregoing portion of the present invention are well known in the art. A disclosure of a video disc player including a detailed description of the foregoing elements and manner of their operation is found in the aforementioned copending U.S. patent application Ser. No. 131,513.

In accordance with the principles of the present invention, a second laser light beam source 84 is provided which emits a second, auxiliary polarized laser light beam 86. This second beam 86 passes through an auxiliary light beam focusing lens 88 to mirrors 90 and 92 which direct the auxiliary laser light beam 86 through the polarizing beam splitter 62 so as to pass through the quarter wavelength plate 64. This beam then passes to the mirror 66 which directs the beam 86 through the objective lens 68 which focuses the beam 86 to a second spot 94 on the surface of the video disc 10. The light from the auxiliary beam 86 reflected off of the video disc 10 passes back through the objective lens 68 and is reflected by mirror 66 through the quarter wavelength plate 64 to the polarizing beam splitter 62. Because it passes twice through the quarter wavelength plate 64, a substantial portion of this light 96 is reflected by the beam splitter 62. A mirror 98 is placed in the path of the reflected light beam 96 which directs the light beam 96 to a photodetector subsystem 100.

The operation of the embodiment of the present invention just disclosed will now be described.

Figures 4, 5:
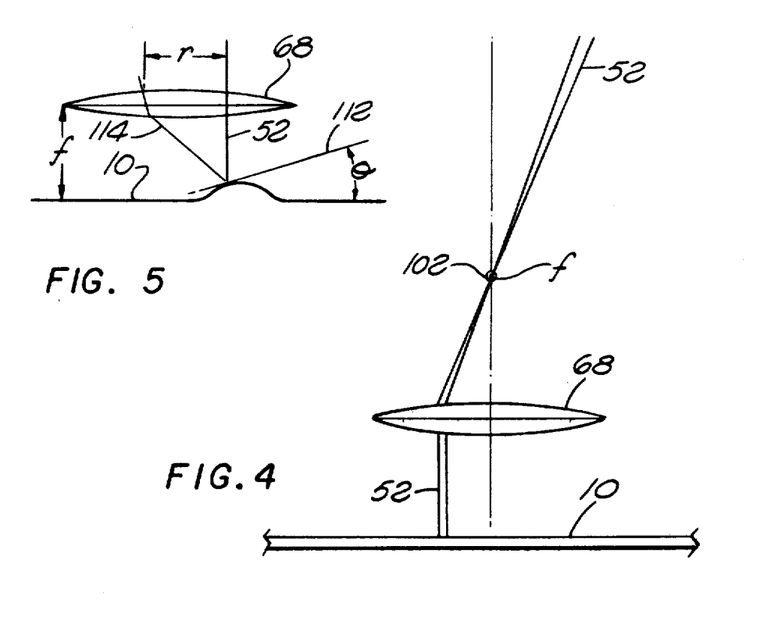
FIG. 4 is a lens diagram showing the incident light beam of the present invention.
FIG. 5 is a lens diagram depicting the incident and reflected light beam of the present invention off of a defect.

Referring now to FIG. 4, a simplified diagram is shown of the objective lens 68 and the video disc 10. As can be seen, the incident auxiliary beam of laser light 52 converges due to the focusing action of the auxiliary beam focusing lens 88 (FIG. 4) to a focal point 102 which, by appropriate selection and arrangement of the focusing lens 88, using well-known techniques, is made to coincide with the focal point f of the objective lens 68 on the opposite side of the lens 68 from the video disc 10. This causes the light beam 52 which emerges from the objective lens 68 to be a collimated beam of light parallel with the central axis of the lens. By thus orienting and collimating the light beam 52 which is incident on the disc 10, the size and location of the spot formed by the beam 52 on the disc 10 remain constant despite any variation in the spacing between the objective lens 68 and the disc 10 which might occur.

If the reflective surface of the video disc 10 is completely flat, the incident light beam 52 will be reflected off of the disc 10 and be directed back along the same path as the incident beam. Thus, in FIG. 4 the light beam 52 represents both the incident and the reflected light beam from a completely flat surface.

Referring now to FIG. 5, a simplified diagram of the objective lens 68 and the surface of the video disc 10 is shown in connection with the presence of a defect 110 shown greatly enlarged as to scale for the purposes of clarity of discription. Also for purposes of clarity, light beams are depicted as single lines.

As shown, the light beam 52 is incident on the sloping side surface of the defect 110. The tangent of the surface of the defect 110, is depicted by line 112 which makes an angle $\theta$ with respect to the flat surface of the disc 10. The reflected beam 114 forms an angle of $2\theta$ with respect to the incident light beam 52. Thus the lateral deflection "r" of the light beam at the pupil plane of the objective lens 6 is given by:

$$r = 2\theta s$$

where s is equal to the distance of the pupil plane of the objective lens 68 from the surface of the video disc 62. A representative value of s for a conventional video disc player is approximately 8.2 mm. For such a configuration, $$r = 16.4 4\theta \text{ (mm)}$$

Figure 6:
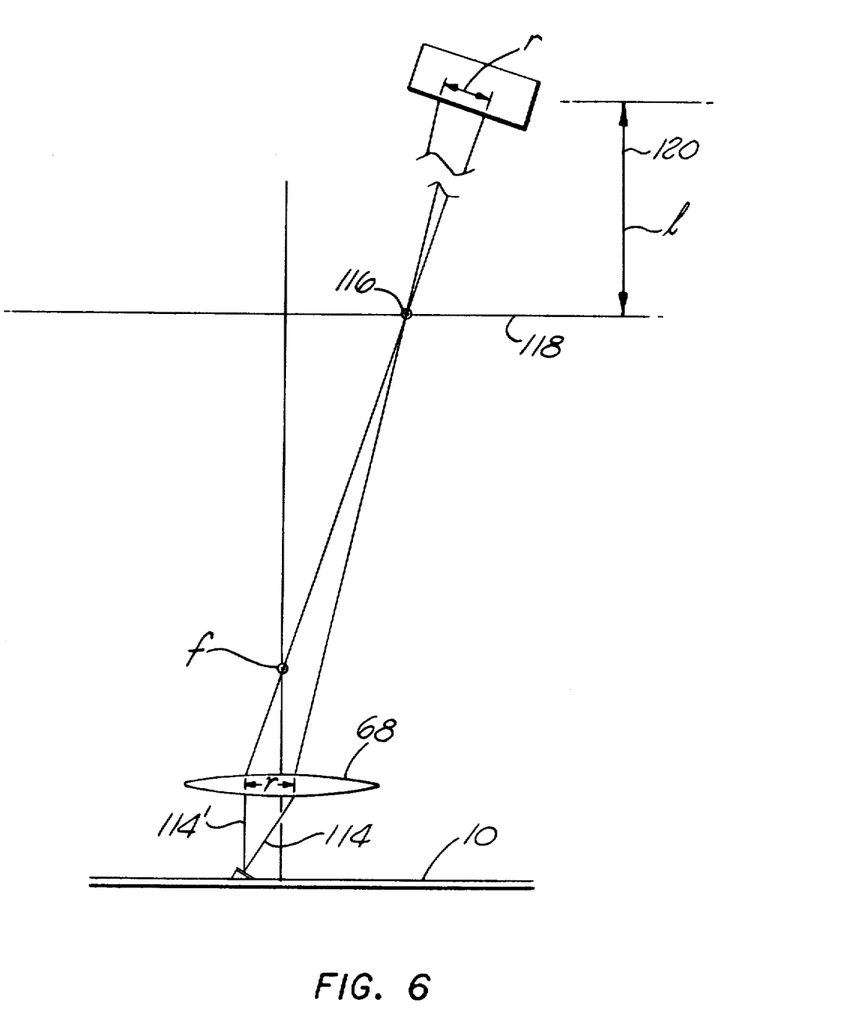
FIG. 6 is a schematic diagram depicting the reflected light beam from the scanned surface along two different paths.

FIG. 6 is a schematic diagram showing the relationship between the objective lens 68, the surface of the video disc 10, and the photodetector subsystem 100. The beam of reflective light 114 is shown deflected by the distance r at the objective lens 68, as described above in connection with FIG. 5. The path of the reflected light beam 114 in the case where no defect is present and reflection is normal to the reflective surface of the disc 10 is also shown for reference.

As can be seen, the reflected beam 114 and 114' converge on a point 116 located at the back image plate 118 of the objective lens 68. The beams then diverge and impinge on the photodetector subsystem 100, as shown. The photodetector subsystem 100 is located a distance 1 from the back image plane 118, as shown by arrow 120. This distance 1 is equal to the long conjugate of the objective lens 10. Because the photodetector subsystem 100 is located at this distance from the back image plane 118, it is in a 1:1 conjugate relationship with the lens and, consequently, any lateral deflection r at the objective lens 68 due to deflection of the reflected light beam 114 will give rise to a corresponding lateral deflection r of the incident light beam 114 on the photodetector subsystem 100, as shown.

Figure 7:
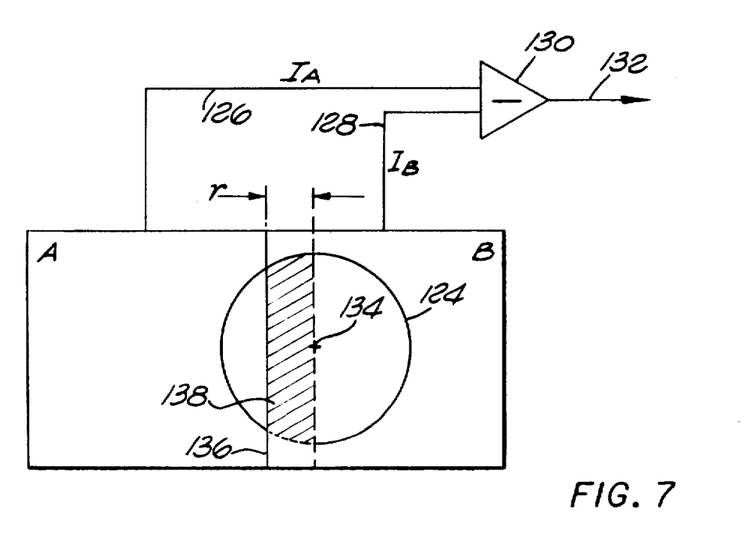
FIG. 7 is a schematic diagram of a light beam detector used in the present invention.

FIG. 7 is a schematic diagram of the photodetector subsystem 100 shown in FIG. 3. A split (bi-cell) photodetector 122 is provided, having a left cell A and a right cell B. This photodetector 122 may be a quadrature photodetector having each of the left and right quadrant cells connected together electrically to provide a split cell function. This permits measurement of the lateral deviation of the light beam incident on the photodetector 122 in one direction. In the preferred embodiment, lateral deflections of the light beam 114 corresponding to defect slopes in the tangential direction are detected, while defect slopes in the radial direction are not detected. It has been found that motions induced in one or more of the optical elements of the video disc player, for example, mirror 66 (FIG. 3) by the action of the radial tracking error servo system give rise to motions of the incident auxiliary laser beam 86. These motions of the beam 86 result in lateral motions of the light beam spot on the photodetector 122 (FIG. 7) which cause false defect signals in the radial direction. Accordingly, the preferred embodiment of the present invention only detects defects in the tangential direction. It should be understood, however, that in the absence of such induced beam motion errors in the radial direction, defect detection may be effected in the radial direction by the appropriate arrangement of a split detector or by the provision of a quadrant photodetector.

Returning now to FIG. 7, the circular boundary 124 of a spot of light incident on the photo cell 122 is shown, off-set by the distance r from the line of separation between Cell A and Cell B. It will be recalled that the distance r represents the lateral deviation of the reflected beam of light at the pupil plane of the objective lens 68, described above in connection with FIG. 5. It will also be appreciated that small spots of light do not have well defined boundaries due to diffraction and other effects. Following convention, it will be assumed that the circular boundary 124 represents the $1/e^2$ light intensity boundary of a spot of light.

The presence of light on cells A and B give rise to currents $I_A$, $I_B$ on output signal lines 126, and 128, respectively. Signal lines 126 and 128 are connected to the inputs of a differential amplifier 130 which produces an output on signal line 132 proportional the difference between signals $I_A$ and $I_B$. It will be appreciated that when the center 134 of the incident beam coincides with the boundary 136 between cell A and cell B of the photodetector 122 currents $I_A$ and $I_B$ are equal and the differential amplifier 120 produces no output. However, if the beam is deflected, for example, to the right as shown in FIG. 7, one cell receives proportionately more light than the other. This is represented in the figure by the cross hatched area 138 in the Figure.

The output on line 132 from the differential amplifier 130 is proportional to twice the amount of light falling on the cross hatched area 138. Therefore, knowing the distribution of light within the boundary 124 of the spot, the performance characteristics of the photodetector 122, and the electrical characteristics of the differential amplifier 130, a quantitative measurement of the dimension r may be made based on the magnitude of the output signal on line 132. If the size of the spot 94 (FIG. 3) on the video disc 10 is small with respect to the dimension of the detected defect, then $\theta$ may be computed as well using the formula $r = 2\theta s$, explained above. Thus, a very accurate measurement of the size of a defect can be made. These calculations are well within the scope of one skilled in this art.

Returning now to FIG. 3, it can be seen that by appropriate placement of mirror 92, with respect to the central axis of the first laser beam, spot 94 may be located on the disc 10 wherever desired with respect to the spot 70 of the first laser beam, limited by the field of view of the objective lens 68 and the radial dimensions of the first laser beam 52 at the location of the deflecting mirror 92. This radial dimension may be made to be quite small by placing the deflecting mirror 92 close to the focal point of the diverging lens 60 where the radial dimensions of the laser beam 52 reach a minimum. In the preferred embodiment of the present invention, the placement of the deflecting mirror 92 is adjusted so that the center of the auxiliary laser beam spot 94 is located at a distance of approximately 0.1 to 0.2 mm from the spot 70 of the first laser beam 52 radially in the direction of forward reading of the first laser beam 52. Thus, if the apparatus reads by advancing the laser beam spot 70 outwardly in a spiralling fashion, the center of the spot 94 is spaced approximately 0.15 mm from the center of spot 70 in the radial direction and toward the outside of the disc.

In addition, the ratio of the focal lengths of the auxiliary beam converging lens 88 to the objective lens 68 in the preferred embodiment of the present invention is selected, according to well-known principles, to produce a spot 94 having a diameter of approximately 80 microns. It has been found that the combination of a spot diameter of 80 microns and a radial spacing of approximately 0.15 mm between the spots 70 and 94, as described above, permits the video disc 72 to be read rapidly in a "fast scan mode" and, upon the detection of a defect, the video disc player can automatically switched to a "read mode" without the necessity of backing up the objective lens. The previously detected defect area may then simply be read by the first laser spot 70 and the video picture viewed to determine if the defect gives rise to unacceptable disruptions in the video picture.

It will be appreciated from the foregoing that the present invention represents a significant advance in the field of defect detection in optical discs. In particular, the invention provides an effective apparatus for providing an accurate measurement of size and location of defects in the reflective surface of optical discs with respect to a reading or writing laser beam spot on the disc. This permits much less time consuming quality control in video optical disc manufacture and also permits defective optical discs to be used as computer data storage elements through the accurate placement of appropriate codes in affected information tracks as defects are detected in the disc and the data are "written" therein. In addition, the apparatus is readily adaptable to existing laser beam reading or writing apparatus with a minimum of modification.

Although the invention has been described in detail with respect to its presently preferred embodiment, it would be understood by one of ordinary skill in the art that various modifications can be made without departing from the spirit of the scope of the invention. Accordingly, it is not intended that the invention be limited except as by the appended claims.

I claim:

1. A beam scanning apparatus for detecting a property of a light beam reflected from a surface to be scanned, comprising:
   (a) a focusing lens disposed a distance from said surface and having its central axis perpendicular to said surface;
   (b) means for maintaining a predetermined substantially fixed distance between said focusing lens and said surface;
   (c) scanning means for providing lateral movement between said lens and said surface;
   (d) first light beam means for providing a first light beam disposed in a nonparallel relationship with the central axis of said lens, said light beam being directed to pass through said lens to said surface, the axis of said first light beam passing through the focal point of said lens located on the opposite side of said lens from said surface; and
   (e) light beam sensing means for detecting a spatial property of that portion of said light beam reflected off of said surface and transmitted back through said lens.

2. A light beam scanning apparatus according to claim 1 wherein said first light beam sensing means comprises means for detecting movement of said reflected beam in at least one lateral direction with respect to the axis of said reflected beam.

3. A beam scanning apparatus according to claim 1 wherein said means for maintaining a substantially fixed distance comprises:
   (a) second light beam means for providing a second light beam parallel with the central axis of said lens and directed to said surface through said lens;
   (b) beam separating means disposed in the path of said second light beam for passing a substantial portion of the light of said second light beam means directed towards said surface and for reflecting to a first detecting location a substantial portion of the light of said second light beam means reflected off of said surface back through said lens;
   (c) second light beam sensing means disposed at said first detecting location for detecting a property of said reflected second light beam which varies with the distance between said lens and said surface and for providing an output signal representative thereof; and
   (d) position control means responsive to said output signal for maintaining said lens at substantially said predetermined fixed distance from said surface.

4. A beam scanning apparatus according to claim 3 wherein said first and said second light beam means provide light beams polarized in one direction, and wherein said beam separating means comprises
   (a) a polarizing beam splitter disposed obliquely with respect to the axis of said second beam; and
   (b) a quarter wavelength plate disposed between said polarizing beam splitter and said surface.

5. A beam scanning apparatus according to claim 4 wherein said first light beam means provides said first light beam so as to pass substantially through said beam splitting means adjacent said second light beam and such that a substantial portion of said first light beam reflected back through said lens is reflected to a second detecting location.

6. A beam scanning apparatus, comprising:
   (a) first light beam means for providing a first beam of light;
   (b) focusing means for focusing said first beam of light onto a surface to be scanned, said focusing means having its axis perpendicular to said surface;
   (c) first detecting means for detecting the light from said focused beam reflected from said surface and transmitted back through said focusing means;
   (d) scanning means for providing relative motion between said focusing means and said surface;
   (e) second light beam means for providing a second beam of light directed to enter said focusing means along an axis spacially distinct from the axis of said first beam as it enters said focusing means, said axis of said second beam of light passing substantially through the focal point of said focusing means opposite said surface; and
   (f) second detecting means, positioned adjacent the optical path of the light of said first beam transmitted back through said focusing means, for intercepting the light of said second light beam means which is reflected from said surface and transmitted back through said focusing means and for providing a signal representative of the angular displacement of a surface irregularity from the plane of said surface being scanned.

7. Apparatus according to claim 6 wherein said second detecting means comprises a photodetector.

8. Apparatus according to claim 7 wherein said photodetector is provided with two sensing surfaces, each having a separate output, such that lateral displacement of said reflected second beam is detectable by said second means.

9. Apparatus according to claim 7 wherein said photodetector comprises a quadrant photodetector, such that lateral displacements of said second reflected beam in two orthogonal directions are detectable by said second detecting means.

10. A method for detecting defects in a surface to be scanned, comprising the steps of:
   (a) providing a focusing lens at a predetermined location with respect to said surface and having its central axis perpendicular to said surface;
   (b) maintaining a substantially fixed distance between said focusing lens and said surface;
   (c) providing lateral movement between said lens and said surface;
   (d) providing a light beam disposed in a non-parallel relationship with the central axis of said lens;
   (e) directing said light beam to pass through said lens to said surface, said light beam being directed such that the axis thereof passes through the focal point of said lens located on the opposite side of said lens from said surface; and
   (f) detecting a spatial property of that portion of said light beam reflected off of said surface and transmitted back through said lens.

11. A method according to claim 10 wherein said step of detecting is performed by detecting movement of said reflected beam in at least one lateral direction with respect to the axis of said reflected beam.

12. A method according to claim 10 wherein said step of providing a first light beam is performed by focusing said light beam at said focal point of said lens.

13. A method for detecting defects according to claim 12 wherein said steps of providing said first light and said second light beam are performed by providing said light beams polarized in one direction, further comprising the steps of:
   (a) providing a polarizing beam splitter disposed obliquely with respect to the access of said second beam;
   (b) providing a quarter wavelength plate disposed between said polarizing beam splitter and said surface.

14. A method according to claim 13 wherein said step of providing a first light beam is performed by providing said first light beam so as to pass substantially through said beam splitting means adjacent said second light beam and such that a substantial portion of said first light beam reflected back to said lens is reflected to a second detecting location.

15. A method for detecting defects in a surface to be scanned, comprising the steps of:
   (a) providing a first beam of light;
   (b) focusing said first beam of light, by means of a focusing element, onto a surface to be scanned, said focusing element having its axis perpendicular to said surface;
   (c) detecting the light from said focus beam reflected from said surface and transmitted back through said focusing element;
   (d) providing relative motion between said focusing element and said surface;
   (e) providing a second beam of light directed to enter said focusing element along an axis spatially distinct from the axis of said first beam as it enters said focusing element, said axis of said second beam of light passing substantially through the focal point of said focusing element opposite said surface; and
   (f) detecting, at a position adjacent the optical path of the light of said first beam transmitted back through said focusing element, the light of said second light beam which is reflected from said surface and transmitted back through said focusing element, and providing a signal representative of the angular displacement of a surface irregularity from the plane of said surface being scanned.

16. A method according to claim 15 wherein said step of detecting the reflected light of said first beam is performed by detecting a property of said beam representative of the state of focus of said first beam on said surface.

17. A method according to claim 15 further comprising the step of focusing said second light beam at said focal point of said focusing element.

* * * * *